US00PP36262P2

(12) United States Plant Patent
Rose

(10) Patent No.: US PP36,262 P2
(45) Date of Patent: Nov. 26, 2024

(54) BLUEBERRY PLANT NAMED 'LB-1'

(50) Latin Name: *Vaccinium corymbosum*
Varietal Denomination: LB-1

(71) Applicant: Samuel Steele Rose, Ivanhoe, NC (US)

(72) Inventor: Samuel Steele Rose, Ivanhoe, NC (US)

( * ) Notice: Subject to any disclaimer, the term of this patent is extended or adjusted under 35 U.S.C. 154(b) by 0 days.

(21) Appl. No.: 18/586,497

(22) Filed: Feb. 25, 2024

(51) Int. Cl.
*A01H 6/36* (2018.01)
*A01H 5/08* (2018.01)

(52) U.S. Cl.
USPC ..... Plt./157

(58) Field of Classification Search
USPC ..... Plt./156, 157
See application file for complete search history.

(56) References Cited

U.S. PATENT DOCUMENTS

PP32,184 P2 * 9/2020 Brazelton ..... A01H 6/368
Plt./157

* cited by examiner

*Primary Examiner* — Karen M Redden
(74) *Attorney, Agent, or Firm* — C. Anne Whealy

(57) ABSTRACT

A new and distinct cultivar of Blueberry plant named 'LB-1', characterized by its upright and bushy plant habit; vigorous growth habit and rapid growth rate; freely branching habit; freely flowering habit with relatively high fruit yield; fruits that can be easily harvested by hand or machine; fruits that are spherical and uniform in size; unique fruit flavor that is slightly peach-like; firm fruit texture and resistance to splitting; good storage, frozen storage and fruit postharvest longevity; and relative tolerance to freezing temperatures.

2 Drawing Sheets

Figure 1:
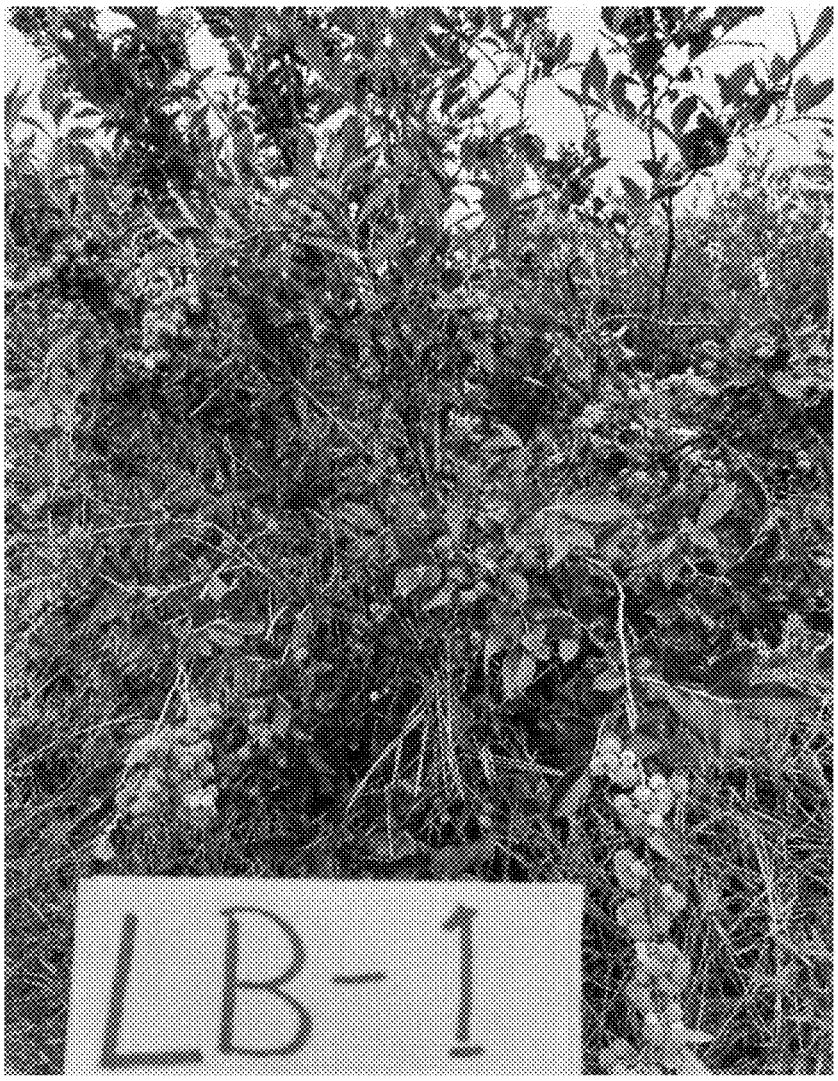

Botanical designation: *Vaccinium corymbosum.*
Cultivar denomination: 'LB-1'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claim a prior art exception under 35 U.S.C. 102(b)(1) for disclosure and/or sales prior to the filing date but less than one year prior to the effective filing date.

BACKGROUND OF THE INVENTION

The present Invention relates to a new and distinct cultivar of Blueberry plant, commonly referred to as a Southern Highbush Blueberry, botanically known as *Vaccinium corymbosum* and hereinafter referred to by the name 'LB-1'.

The new Blueberry plant is a product of a planned breeding program conducted by the Inventor in Ivanhoe, North Carolina. The objective of the breeding program was to develop new vigorous Blueberry plants with large fruits and good fruit quality, productivity, uniformity and postproduction longevity.

The new Blueberry plant originated from an open-pollination in 2015 in Ivanhoe, North Carolina by the Inventor of an unidentified selection of *Vaccinium corymbosum*, not patented as the female, or seed, parent with an unknown selection of *Vaccinium corymbosum*, not patented, as the male, or pollen, parent. The new Blueberry plant was discovered and selected by the Inventor as a single plant from within the progeny of the stated open-pollination in a controlled outdoor nursery environment in Ivanhoe, North Carolina in 2015.

Asexual reproduction of the new Blueberry plant by softwood cuttings in a controlled environment at Ivanhoe, North Carolina since 2015 has shown that the unique features of this new Blueberry plant are stable and reproduced true to type in successive generations of asexual reproduction.

SUMMARY OF THE INVENTION

Plants of the new Blueberry have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'LB-1'. These characteristics in combination distinguish 'LB-1' as a new and distinct Blueberry plant:

1. Upright and bushy plant habit.
2. Vigorous growth habit and rapid growth rate.
3. Freely branching habit.
4. Freely flowering habit with relatively high fruit yield.
5. Fruits can be easily harvested by hand or machine.
6. Fruits are spherical and uniform in size.
7. Unique fruit flavor that is slightly peach-like.
8. Firm fruit texture and resistant to splitting.
9. Good storage, frozen storage and fruit postharvest longevity.
10. Relatively tolerant to freezing temperatures.

Plants of the new Blueberry differ primarily from plants of the unidentified female parent selection in the following characteristics:

1. Plants of the new Blueberry are more vigorous than the female parent selection.
2. Fruits of plants of the new Blueberry remain on the plant longer than fruits of plants of the female parent selection.

Plants of the new Blueberry can be compared to plants of *Vaccinium corymbosum* 'O'Neal', not patented. In side-by-side comparisons, plants of the new Blueberry differ from plants of 'O'Neal' in the following characteristics:

1. Plants of the new Blueberry are more upright than and not as outwardly spreading as plants of 'O'Neal'.
2. Plants of the new Blueberry are more vigorous than plants of 'O'Neal'.
3. Leaves of plants of the new Blueberry are darker green in color than leaves of plants of 'O'Neal'.
4. Plants of the new Blueberry are more freely flowering than plants of 'O'Neal'.
5. Plants of the new Blueberry produce more fruits per plant than plants of 'O'Neal'.

BRIEF DESCRIPTION OF THE PHOTOGRAPHS

The accompanying colored photographs illustrate the appearance of the new Blueberry plant showing the colors as true as it is reasonably possible to obtain in colored reproductions of this type. Colors in the photographs may differ slightly from the color values cited in the detailed botanical description which accurately describe the colors of the new Blueberry plant.

The photograph on the first sheet (FIG. 1) is a side perspective view of a typical fruiting plant of 'LB-1'.

Figure 2:
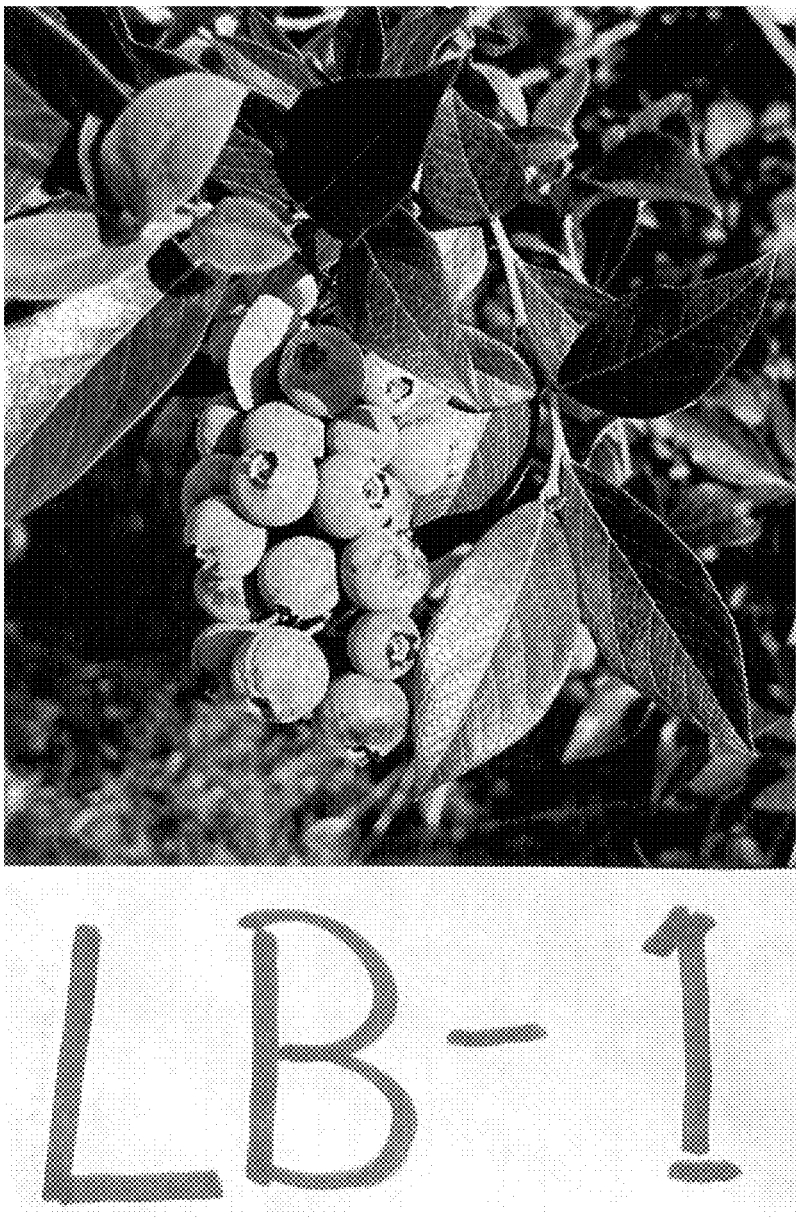

The photograph on the second sheet (FIG. 2) is a close-up view of typical fruits of 'LB-1' on the plant.

DETAILED BOTANICAL DESCRIPTION

The aforementioned photographs, following observations and measurements describe plants grown during the spring, summer and autumn in ground beds in an outdoor nursery in Ivanhoe, North Carolina and under typical cultural practices of Blueberry plant production. During the production of the plants, day temperatures averaged 27.7° C. and night temperatures averaged 10° C. Plants were two years old when the photographs and description were taken. In the following description, color references are made to The Royal Horticultural Society Colour Chart, 2019 Edition, except where general terms of ordinary dictionary significance are used.

Botanical classification: *Vaccinium corymbosum* 'LB-1'.

Parentage:

*Female, or seed, parent*.—Unidentified selection of *Vaccinium corymbosum*, not patented.

*Male, or pollen, parent*.—Unknown selection of *Vaccinium corymbosum*, not patented.

Propagation:

*Type*.—By soft wood cuttings.

*Time to initiate roots, summer*.—About four to five weeks at temperatures about 26.6° C.

*Time to produce a rooted young plant, summer*.—About six to eight weeks at temperatures about 23.6° C.

*Root description*.—Fine in thickness, fibrous, typically close to 163A in color; actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright and bushy plant habit; vigorous growth habit and rapid growth rate; plants produce fruit on one-year old shoots only.

*Plant height*.—About 148 cm.

*Plant diameter*.—About 91 cm.

Branch description:

*Quantity per plant*.—Freely branching habit with about five primary branches each primary branch with about five secondary branches.

*Length*.—About 45.7 cm.

*Diameter*.—About 5 mm.

*Internode length*.—About 2 cm.

*Strength*.—Strong.

*Aspect*.—About 25 to 45 degrees From vertical.

*Texture and luster*.—Smooth, glabrous; semi-glossy.

*Color, developing*.—Close to 145B.

*Color, developed*.—Close to 145A; if woody, close to 196B.

Leaf description:

*Arrangement*.—Alternate; simple.

*Length*.—About 5.8 cm to 8 cm.

*Width*.—About 2.8 cm to 3.4 cm.

*Shape*.—Elliptical.

*Apex*.—Acute, pointed.

*Base*.—Tapering, cuneate; asymmetrical.

*Margin*.—Entire, not lobed.

*Texture and luster, upper surface*.—Smooth, glabrous; semi-glossy, moderately waxy.

*Texture and luster, lower surface*.—Prominent mid-vein, glabrous; matte, not waxy.

*Venation*.—Pinnate and reticulate.

*Color*.—Developing leaves, upper surface: Close to 145A. Developing leaves, lower surface: Close to 145B. Fully expanded leaves, upper surface: Close to 147A; venation, close to 145B. Fully expanded leaves, lower surface: Close to 138D; venation, close to 145C.

*Petioles*.—Length: About 2 mm to 6 mm. Diameter: About 0.75 mm to 1.25 mm. Strength: Moderately strong. Texture and luster, upper and lower surfaces: Smooth, glabrous; semi-glossy. Color, upper surface: Close to 145B. Color, lower surface: Close to 61D.

Flower description:

*Flower form and flowering habit*.—Single urceolate-shaped flowers arranged in racemes; freely flowering with about nine flowers per inflorescence and about 4,500 to 5,500 flowers developing per plant during the flowering season; flowers face mostly outwardly; flowers not persistent.

*Fragrance*.—Fragrant, sweet.

*Natural flowering season*.—In Ivanhoe, North Carolina, plants typically flower from early March to mid-May.

*Flower buds*.—Length: About 4 mm. Diameter: About 3 mm. Shape: Ovoid. Texture and luster: Smooth, glabrous; glossy. Color: Close to 178A.

*Inflorescence height*.—About 1.7 cm.

*Inflorescence diameter*.—About 2.5 cm.

*Flower diameter*.—About 7 mm by 10 mm.

*Flower depth* (*height*).—About 9 mm.

*Petals*.—Arrangement: Five petals, fused. Length: About 9 mm. Shape: Urceolate. Apex: Cuspidate. Margin, distal free part: Entire. Texture and luster, upper and lower surfaces: Smooth, glabrous; matte. Color: When opening, upper and lower surfaces: Close to N155C. Fully opened, upper and lower surfaces: Close to N155C; venation, close to N155C.

*Sepals*.—Arrangement: Five sepals, fused. Length: About 4 mm. Width: About 5 mm. Shape: Roughly deltoid. Apex: Acute. Margin, free part: Entire. Texture and luster, upper surface: Smooth, glabrous; semi-glossy. Texture and luster, lower surface: Smooth, glabrous; matte. Color, upper surface: Close to 150B. Color, lower surface: Close to 150C.

*Peduncles*.—Length: About 7 mm. Diameter: About 1 mm. Strength: Strong. Texture and luster: Smooth, glabrous; matte. Color: Close to 144A.

*Pedicels* (*flowers and fruits*).—Length: About 3 mm to 4 mm. Diameter: About 0.3 mm. Strength: Strong. Texture and luster: Smooth, glabrous; matte. Color: Close to 144A.

*Reproductive organs*.—Stamens: Quantity per flower: About seven to ten. Filament length: About 2 mm. Filament color: Close to 154D. Anther size: About 0.25 mm by 1 mm. Anther shape: Oblong. Anther color: Close to 164A. Pollen amount: Abundant. Pollen color: Close to 5C. Pistils: Quantity per flower: One. Pistil length: About 1 cm. Stigma diameter: About 0.5 mm. Stigma shape: Rounded. Stigma color: Close to 151A. Style length: About 9.75 mm. Style color: Close to 151A. Ovary color: Close to 144A.

*Fruits*.—Type: Berry; sepals, erect. Quantity: One per flower. Time to ripening: Depending on temperatures, about one to two weeks. Keeping quality: Good postproduction longevity, about three to four weeks; fruits have been observed to tolerate frozen storage extremely well. Size: About 1.5 cm by 1.5 cm. Diameter of calyx basin: About 5 mm. Depth of calyx basin: About 0.6 mm. Weight: About 2.36 g. Shape: Spherical. Firmness: Firm; resistant to splitting; about 192 g/mm. Texture and luster: Smooth, glabrous; somewhat glossy. Flesh color: Close to 157A. Skin color, developed, with waxy bloom: Close to 98D. Skin color, developed, without waxy bloom: Close to 202A. Taste: Unique fruit flavor that is slightly peach-like; brix, close to 8.6%; medium acidity.

*Seeds*.—Quantity: About 22 per berry. Length: About 2.1 mm. Diameter: About 0.8 mm. Texture and luster: Smooth, glabrous; matte. Color: Close to 167B.

Pathogen & pest resistance: To date, plants of the new Blueberry have been observed to be resistant to pathogens and pests common to Blueberry plants.

Temperature tolerance: Plants of the new Blueberry have been observed to tolerate temperatures ranging from about −9.4° C. to about 37.2° C. and to be suitable for USDA Hardiness Zone 8A.

It is claimed:

1. A new and distinct Blueberry plant named 'LB-1' as illustrated and described.

* * * * *